(12) United States Patent
Ivanov et al.

(10) Patent No.: US 10,736,872 B1
(45) Date of Patent: *Aug. 11, 2020

(54) PHARMACEUTICAL MIXTURE TO TREAT STATIN INDUCED VASCULAR CALCIFICATION

(71) Applicant: Matthias W Rath, Aptos, CA (US)

(72) Inventors: Vadim O Ivanov, Castro Valley, CA (US); Matthias W Rath, Aptos, CA (US); Aleksandra Niedzwiecki, Aptos, CA (US)

(73) Assignee: Matthias W. Rath, Aptos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/853,519

(22) Filed: Apr. 20, 2020

Related U.S. Application Data

(62) Division of application No. 16/562,313, filed on Sep. 5, 2019.

(51) Int. Cl.

| | | |
|---|---|---|
| *A61K 31/375* | (2006.01) | |
| *A61K 31/366* | (2006.01) | |
| *A61K 31/51* | (2006.01) | |
| *A61K 31/675* | (2006.01) | |
| *A61K 31/4188* | (2006.01) | |
| *A61K 31/197* | (2006.01) | |
| *A61K 31/455* | (2006.01) | |
| *A61K 31/525* | (2006.01) | |
| *A61K 31/22* | (2006.01) | |
| *A61K 31/205* | (2006.01) | |
| *A61K 31/355* | (2006.01) | |
| *A61K 31/714* | (2006.01) | |
| *A61P 9/10* | (2006.01) | |
| *A61K 31/519* | (2006.01) | |

(52) U.S. Cl.
CPC .......... *A61K 31/375* (2013.01); *A61K 31/197* (2013.01); *A61K 31/205* (2013.01); *A61K 31/22* (2013.01); *A61K 31/355* (2013.01); *A61K 31/366* (2013.01); *A61K 31/4188* (2013.01); *A61K 31/455* (2013.01); *A61K 31/51* (2013.01); *A61K 31/519* (2013.01); *A61K 31/525* (2013.01); *A61K 31/675* (2013.01); *A61K 31/714* (2013.01); *A61P 9/10* (2018.01)

(58) Field of Classification Search
CPC ... A61K 31/375; A61K 31/197; A61K 31/205
See application file for complete search history.

(56) References Cited

U.S. PATENT DOCUMENTS

2013/0115281 A1* 5/2013 Draper ................. A61K 9/5084
424/452

OTHER PUBLICATIONS

Samadikhah (Advanced Pharmaceutical Bulletin, 2014, 4(1), 97-100).*

* cited by examiner

*Primary Examiner* — Pancham Bakshi
(74) *Attorney, Agent, or Firm* — Geeta Kadambi; Riddhi IP LLC

(57) ABSTRACT

A pharmaceutical composition in a physiological dose for a mammal is used for reducing vascular calcification caused due to statin consumption. The composition contains mixture 1 and statin. The mixture 1 contains combination of the Vitamin C, Vitamin E, Vitamin B1, Vitamin B2, Vitamin B3, Vitamin B5, Vitamin B6, Vitamin B12, Folic acid, Biotin, L-carnitine and Betaine. The mixture 1 can be used as a stand-alone product with or without statin.

10 Claims, 5 Drawing Sheets

PHARMACEUTICAL MIXTURE TO TREAT STATIN INDUCED VASCULAR CALCIFICATION

CROSS REFERENCE TO RELATED APPLICATION

This application is a divisional application of an U.S. patent application Ser. No. 16/562,313 filed on Sep. 5, 2019 and claims priority of the same. The disclosure is hereby incorporated by this reference in its entirety for all of their teachings.

FIELD OF TECHNOLOGY

The present invention relates to a mixture of natural ingredients for preventing or mitigating the vascular calcification induced by statins.

BACKGROUND

Statin the ubiquitous medication is prescribed to many patients and they do have side effects. Upon treatment with statins, patients exhibit side effects including muscle pain, increased risk of diabetes mellitus, and abnormal blood levels of liver enzymes. In some patients, for example lovastatin leads to myopathy and asymptomatic, but marked and persistent increases in liver transaminases.

It has furthermore been known that statins increase vascular calcifications, which are a recognized risk factor for heart disease (Ikegami Y, et. al. 2018). In the recent analysis of 8 prospective randomized trials using serial coronary intravascular ultrasound, Puri et al. (Puri R, et. al. 2015) concluded that independent of their plaque-regressive effects, statins promote coronary atheroma calcification.

Still there is a controversy between arterial calcification being a well-established marker and prognoses index for cardiovascular disease development, statins stimulating effects on arterial calcification and apparent beneficial effects of statin supplementation on clinical events in CVD patients. Some researchers are providing a tending plausible explanation of these conflicting evidences to be a "special" mechanism of arterial calcification under statin treatments which results in greater lesion stability defined as fewer VH-thin-cap fibroatheromas and plaque ruptures and more calcified thick-cap fibroatheromas.

Vascular calcification is a relevant pathophysiological process that is associated with coronary atherosclerosis, and is a prognostic marker of cardiovascular morbidity and mortality. Vascular smooth muscle cells (SMC) have an extraordinary capacity to undergo osteoblastic phenotypical differentiation. Calcification of the intimal and/or medial vascular cell layer leads to differentiation of osteoblasts whether from a smooth muscle cell, a mesenchymal cell, or vascular pericyte, characterized, among others, by increased alkaline phosphatase activity, osteocalcin production and bone matrix secretion. Biochemical mechanisms associated with the conversion of SMC into osteoblastic cells have been elaborated; however the decisive mechanisms of what triggers and/or regulates this process have remained largely elusive.

Recent studies showed that plaque calcification is a dynamic process and related to the degree of vascular inflammation. Several inflammatory factors produced during the different phases of atherosclerosis can induce the expression and activation of osteoblastic cells located within the arterial wall, which, in turn, promote deposition of calcium.

The presence of regulatory proteins along with dedifferentiated osteoblast-like cells was demonstrated to originate from vascular smooth muscle cells (VSMCs) that were designated calcifying vascular cells. These cells are implicated in the synthesis/reabsorption of bone in atherosclerotic plaques, especially around calcification. Thus, it has been proposed that bone cell function in the vascular wall is, in some aspects, similar to that in bones. However, in vitro studies provided evidence that regulation of bone synthesis in the vascular wall and in the skeleton are different. When stimulated by oxidative stress or with oxidized LDL, osteoblasts of the skeleton and CVCs (a population of vascular cells with osteoblastic characteristics) showed opposing response, a decrease and increase of bone formation, respectively.

SUMMARY

The object underlying the present invention is to treat or prevent or reduce the vascular calcification induced in patients by administration of statins using pharmaceutical composition mixture 1 with statin. In one embodiment, mixture 1 with statin for use in treating patients receiving statin treatment. In another embodiment, mixture 1 for use in treating or preventing vascular calcification in patients. In another embodiment, L-ascorbic acid or ascorbate is used in treating or preventing the vascular calcification induced in patients by administration of statins. The use of L-ascorbic acid or ascorbate for mitigating the vascular calcification induced by statins.

A vascular calcification reducing pharmaceutical composition mixture 1 containing a Vitamin C, Vitamin E, Vitamin B1, Vitamin B2, Vitamin B3, Vitamin B5, Vitamin B6, Vitamin B12, Folic acid, Biotin, L-carnitine and Betaine with statin in a dosage form that allows for administering to a patient. A pharmaceutical composition mixture 1 containing at least one statin in a dosage form with nutrients in the mixture 1 that allows for administering as a daily dose to a patient suffering from a cardiovascular disease. The pharmaceutical composition, wherein the at least one statin and mixture 1 or L-ascorbic acid or ascorbate is present as a physical mixture or as separate pharmaceutical compositions intended for administration to a patient. The pharmaceutical composition mixture 1 is used for the prevention or treatment or reduction of the side effects of statin consumption in a patient suffering from a cardiovascular disease. The pharmaceutical composition mixture 1, wherein the cardiovascular disease is coronary artery disease, cerebrovascular disease or peripheral vascular disease.

The pharmaceutical composition, wherein the statin is selected from the group consisting of atorvastatin, cerivastatin, fluvastatin, lovastatin, mevastatin, pitavastatin, pravastatin, rosuvastatin, simvastatin, or mixtures thereof, or any other type or form of statin, or from a combination of the statin with niacin. The pharmaceutical composition, wherein the ascorbate is selected from water-soluble or lipid-soluble ascorbates or mixtures thereof, preferably from calcium ascorbate, magnesium ascorbate, sodium ascorbate, ascorbyl phosphate, ascorbyl palmitate or mixtures thereof.

The pharmaceutical composition mixture 1, additionally may contain coenzyme Q10 in a dosage form that allows for the concomitant administering of the at least one statin, L-ascorbic acid or ascorbate, and coenzyme Q10 to a patient. The pharmaceutical composition, comprising a daily dosage amount of L-ascorbic acid or ascorbate from 10 mg to 100 g, preferably 100 mg to 10 g, and the lowest to the highest commercially available or clinically applicable dose of at least one statin, preferably from 5 mg to 100 mg. The pharmaceutical composition, further comprising one or more additional micronutrients beside L-ascorbic acid or ascorbate, preferably selected from trace minerals, vitamins, and mixtures thereof. The pharmaceutical composition, wherein the one or more additional micronutrients contain niacin, preferably in a mixture with the statin.

A method of treating or preventing or reducing vascular calcification in a patient, who preferably is treated with statins, by administering mixture 1 or L-ascorbic acid or ascorbate to the patient. A method of treating a patient with mixture 1 or L-ascorbic acid or ascorbate, wherein the patient is concomitantly treated with at least one statin. A method of concomitantly administering at least one statin and mixture 1 or L-ascorbic acid or ascorbate to a patient for treating or preventing cardiovascular disease. The method of using mixture 1 or L-ascorbic acid or ascorbate for mitigating the vascular calcification induced by statins.

A pharmaceutical composition containing at least one statin and mixture 1 or L-ascorbic acid or ascorbate in a dosage form that allows for the concomitant administering of the at least one statin and L-ascorbic acid or ascorbate to a patient. The pharmaceutical composition, wherein the at least one statin and mixture 1 or L-ascorbic acid or ascorbate is present as a physical mixture or as separate pharmaceutical compositions intended for concomitant administration to a patient. The pharmaceutical composition for the prevention or treatment of cardiovascular disease is disclosed. The pharmaceutical composition, wherein the cardiovascular disease is coronary artery disease, cerebrovascular disease or peripheral vascular disease.

The pharmaceutical composition, wherein the statin is selected from the group consisting of atorvastatin, cerivastatin, fluvastatin, lovastatin, mevastatin, pitavastatin, pravastatin, rosuvastatin, simvastatin, or mixtures thereof, or any other type or form of statin, or from a combination of the statin with niacin.

The pharmaceutical composition, wherein the vitamin C in the mixture 1 is an ascorbate, wherein the ascorbate is selected from water-soluble or lipid-soluble ascorbates, or mixtures thereof, preferably from calcium ascorbate, magnesium ascorbate, sodium ascorbate, ascorbyl phosphate, ascorbyl palmitate or mixtures thereof. The pharmaceutical composition mixture 1, additionally containing coenzyme Q10 in a dosage form that allows for the concomitant administering of the at least one statin, mixture 1 or L-ascorbic acid or ascorbate, and coenzyme Q10 to a patient.

The pharmaceutical composition mixture 1 contains the nutrients as single physiological dose or per daily dose as follows: Vitamin C (Calcium ascorbate, magnesium ascorbate)—300-1000.2 mg, Vitamin E—27.5 mg-82.5 mg, Vitamin B1—3.3 mg-9.9 mg, Vitamin B2—3.3 mg-9.9 mg, Vitamin B3—115 mg-350.1 mg, Vitamin B5—16.7 mg-50.1 mg, Vitamin B6—3.3 mg-9.9 mg, Vitamin B12—10 µg-30 µg, Folic acid—133.3 ug-399.9 µg, Biotin—33.3 ug-99.9 µg, L-carnitine—33.3 mg-99.9 mg, Betaine—23.3 mg-69.9 mg with statin at 5 mg to 100 mg.

The pharmaceutical composition mixture 1 contains the nutrients as single physiological dose or per daily dose as follows: Vitamin C (Calcium ascorbate, magnesium ascorbate)—300-1000.2 mg, Vitamin E—27.5 mg-82.5 mg, Vitamin B1—3.3 mg-9.9 mg, Vitamin B2—3.3 mg-9.9 mg, Vitamin B3—115 mg-350.1 mg, Vitamin B5—16.7 mg-50.1 mg, Vitamin B6—3.3 mg-9.9 mg, Vitamin B12—10 µg-30 µg, Folic acid—133.3 ug-399.9 µg, Biotin—33.3 ug-99.9 µg, L-carnitine—33.3 mg-99.9 mg, Betaine—23.3 mg-69.9 mg without statin at 5 mg to 100 mg.

The pharmaceutical composition, comprising a daily dosage amount of L-ascorbic acid or ascorbate from 10 mg to 100 g, preferably 100 mg to 10 g, and the lowest to the highest commercially available or clinically applicable dose of the at least one statin, preferably from 5 mg to 100 mg. The pharmaceutical composition, further comprising one or more additional micronutrients beside L-ascorbic acid or ascorbate. The pharmaceutical composition, wherein the one or more additional micronutrients are selected from trace minerals, vitamins, and mixtures thereof, and preferably contain niacin, which can be present in a mixture with the statin. The pharmaceutical composition consisting of a daily dosage amount of L-ascorbic acid or ascorbate from 10 mg to 100 g, preferably 100 mg to 10 g, and the lowest to the highest commercially available or clinically applicable dose of the at least one statin, preferably from 5 mg to 100 mg and one or more additional micronutrients are selected from trace minerals, vitamins, and mixtures thereof, and preferably contain niacin, which can be present in a mixture with the statin.

A method for counteracting statin-associated elevated vascular calcification in a subject in need of such treatment which comprises the concomitant administration of an effective amount of at least one statin and an effective amount of mixture 1 or L-ascorbic acid or ascorbate. A method for counteracting statin-associated elevated vascular calcification in a subject in need of such treatment which consisting of concomitant administration of a physiological dose for a mammal is used for reducing vascular calcification caused due to statin consumption of at least one statin and an effective amount of mixture 1. A method for treating or preventing vascular calcification in a patient which comprises the administration of an effective amount of mixture 1 with statin to the patient.

Finally, the present invention is described further in the detailed description to further illustrate various aspects of the present invention.

BRIEF DESCRIPTION OF THE DRAWINGS

Example embodiments are illustrated by way of example and not limitation in the figures of the accompanying drawings, in which like references indicate similar elements and in which.

Figure 1:
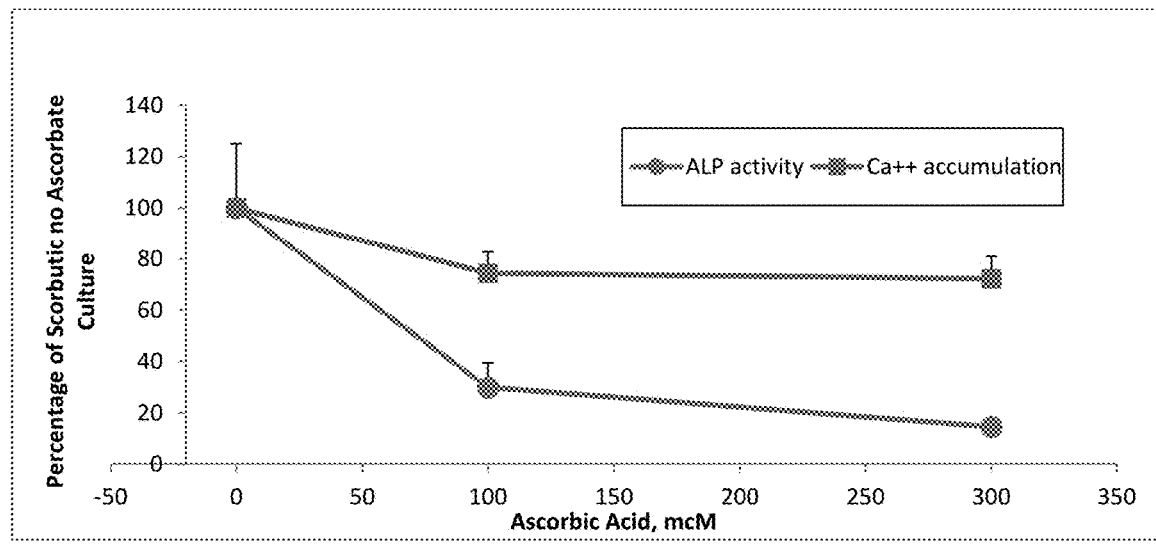
FIG. 1 shows the effects of treatment with ascorbic acid on calcification of extracellular matrix in cultured human aortic smooth muscle cells.

Others features of the present embodiments will be apparent from the accompanying drawings and from the detailed description that follows.

DETAILED DESCRIPTION

According to the present invention, it has been found that mixture 1 or L-ascorbic acid or ascorbate is effective in treating or preventing or reducing the vascular calcification in a human system, especially when co-administered or combined in a dose with statin.

Vitamin C is an essential nutrient for certain animals including humans. Clinical trials have shown a significant positive effect of vitamin C on endothelial function when taken at doses greater than 500 mg per day. Its possible influence on the treatment or prevention of cardiovascular disease has been discussed. Vitamin C is a very powerful antioxidant and is essential for the formation of collagen and optimum extracellular matrix (ECM). It can prevent lipoprotein deposition and development of atherosclerosis by protecting the integrity and strength of the vascular wall.

Our previous studies have shown that ascorbate can inhibit excessive proliferation and migration of SMC in vitro (Ivanov V et. al. 2007). Also, dietary vitamin C is essential in prevention of lipoproteins deposition in the vascular wall and atherosclerosis in genetically engineered mice mimicking human metabolism in respect their inability to produce vitamin C and expressing human lipoprotein (a) (Cha J et. al. 2015). In a clinical study, a daily micronutrient supplementation, including about 4 grams of vitamin C, was able to halt the progression of coronary calcifications in patients diagnosed with early coronary artery disease (Rath M et. al. 1996).

We investigated the effects of vitamin C on vascular SMC, human dermal fibroblasts (DF) as well as on immortalized human fetal osteoblasts (FOB) and the potential of these cells to contribute to vascular calcification. Moreover, we evaluated the role of statins in connection with this regulatory process, in light of the fact that these drugs are currently taken by millions of patients in the expectation that they curb vascular calcification. Thereby, we came to the invention as disclosed herewith.

According to the present invention, vitamin C, also known as ascorbic acid or L-ascorbic acid, is employed. As an alternative, ascorbate can be employed, wherein the ascorbate, a salt of ascorbic acid with bases or acids stronger than ascorbic acid, is preferably selected from water-soluble or lipid-soluble ascorbates or mixtures thereof and is more preferably selected from the group consisting of calcium ascorbate, magnesium ascorbate, sodium ascorbate, ascorbyl phosphate, ascorbyl palmitate or mixtures thereof. The L-ascorbic acid or ascorbate is (preferably) administered to patients that are treated with statins.

Statins are related to a class of lipid-lowering medications that reduce illness and mortality in those who are at high risk of cardiovascular disease. All suitable statins can be employed in the context of the present invention. Preferably, the stain is selected from the group consisting of atorvastatin, cerivastatin, fluvastatin, lovastatin, mevastatin, pitavastatin, pravastatin, rosuvastatin, simvastatin, or mixtures thereof, or any other type or form of statin, or from a combination of the statin with niacin.

According to one aspect of the invention, the L-ascorbic acid or ascorbate and statin can be administered together with one or more additional micronutrients beside L-ascorbic acid or ascorbate. For example, a pharmaceutical composition comprising statin, L-ascorbic acid or ascorbate, and one or more additional micronutrients can be provided for this purpose.

Preferably, the one or more additional micronutrients are administered together with mixture 1 or L-ascorbic acid or ascorbate and with statin. The one or more micronutrients are preferably selected from trace minerals, vitamins different from ascorbate/vitamin C, amino acids and their derivatives, and mixtures thereof. Trace minerals are only required in small amounts (traces) by humans.

Trace minerals are preferably selected from boron, cobalt (preferably as a component of vitamin B12), chromium, copper, iodine, iron, manganese, molybdenum, selenium, zinc, and mixtures thereof.

Vitamins different from vitamin C are preferably selected from vitamin B complex, vitamin B1 (thiamin), vitamin B2 (riboflavin), vitamin B3 (niacin), vitamin B5 (pantothenic acid), vitamin B6 group including pyridoxine, pyridoxal-5-phosphate, and pyridoxamine, vitamin B7 (biotin), vitamin B9 (folate), vitamin B12 (cobalamin), choline, vitamin A (e.g. retinol or provitamin A carotenoids), vitamin D, including ergocalciferol and cholecalciferol, vitamin E (tocopherols and tocotrienols), vitamin K including vitamin K1 (phylloquinone) and vitamin K2 (menaquinone), carotenoids, including alpha carotene, beta carotene, cryptoxanthin, lutein, lycopene and Zeaxanthin.

Amino acids and their derivatives include betaine and L-carnitine. Further micronutrients preferably comprise vitamins B6 and B12, folic acid and betaine. A preferred combination of micronutrients is contained in Mixture 1 as outlined below.

When a patient is treated with statins, the daily dosage amount can be from the lowest to the highest commercially available or clinically applicable dose. The dosage amount is preferably in the range of from 5 to 100 mg, preferred 10 to 80 mg, more preferably 10 to 40 mg, most preferably 10 to 20 mg.

The amount of L-ascorbic acid or ascorbate administered to a patient receiving statin treatment is preferably 10 mg to 100 g, more preferably 100 mg to 10 g, most preferably 200 mg to 5 g daily dosage.

It is possible to administer the L-ascorbic acid or ascorbate (and optional one or more additional micronutrients) simultaneously with the statin, for example in a tablet containing both, L-ascorbic acid or ascorbate (and optional one or more additional micronutrients), and statin. Furthermore, it is possible to administer L-ascorbic acid or ascorbate (and optional one or more additional micronutrients) and statin in separate pharmaceutical compositions, but concomitantly. The term "concomitantly" means that the administration of both active ingredients takes place within a time range of from 0 to 5 hours, preferably 0 to 3 hours, more preferably 0 to 1 hours, based on one administration per day.

Since both statins and L-ascorbic acid or ascorbate (as well as other/additional micronutrients different from vitamin C) are well established for an individual and separate administration to patients in need thereof, the known pharmaceutical or nutritional compositions can be employed according to the present invention while ensuring the concomitant use of both active ingredients.

For example, a micronutrient composition that contains ascorbate and can advantageously be employed in combination with statins is Mixture 1. Mixture 1 contains vitamins, L-carnitine and betaine and can be employed for daily nutritional supplementation. Typically, three tablets are taken for a day (one tablet three times a day at meal times with plenty of liquid (water, juice, tea)).

Mixture 1 contains each nutrient in the physilogocal dose range for One to three tablets for mammals as follows:

Vitamin C (Calcium ascorbate, magnesium ascorbate): 300-1000.2 mg
Vitamin E: 27.5 mg-82.5 mg
Vitamin B1: 3.3 mg-9.9 mg
Vitamin B2: 3.3 mg-9.9 mg
Vitamin B3: 115 mg-350.1 mg
Vitamin B5: 16.7 mg-50.1 mg
Vitamin B6: 3.3 mg-9.9 mg
Vitamin B12: 10 µg-30 µg
Folic acid: 133.3 ug-399.9 µg
Biotin: 33.3 ug-99.9 µg
L-carnitine: 33.3 mg-99.9 mg
Betaine: 23.3 mg-69.9 mg Mixture 1 contains selected micronutrients in a synergistic combination. This reconstructive formula can be combined with other basic formulas, e.g. Vitacor Plus™.

It supplements the spectrum of specific vitamins and other micronutrients with important factors to assist the normal homocysteine and cholesterol metabolism. A tablet contains typically the following ingredients: Vitamin C, cellulose filler, vitamin B3, L-carnitine tartrate 5.26%, release agent stearic acid, betaine hydrochloride 3.24%, vitamin E, vitamin B5, croscarmellose sodium, glazing agent calcium carbonate, maltodextrin, release agent silicon dioxide, glazing agent shellac, vitamin B1, vitamin B6, biotin, coloring agent riboflavin (vitamin B2), coconut oil extract, folic acid, vitamin B2, lemon oil, vitamin B12, natural lemon flavor.

Vitamins B6 and B12, folic acid and betaine are important factors for assisting the normal homocysteine metabolism. Therefore, optimal supply of these micronutrients is essential for maintaining normal homocysteine levels.

The ingredients in pharmaceutical composition mixture 1 supports cellular metabolism in many ways simultaneously, e.g.: a) with betaine, vitamin B6, vitamin B12 and folic acid to support normal homocysteine metabolism; b) with biotin and B vitamins as a contribution to supporting normal energy metabolism; c) with vitamin C and vitamin E as a contribution to protecting the cells against oxidative stress.

The recommended daily dose can be as indicated above, or can be 10 to 300%, preferably 20 to 200%, more preferably 50 to 150% thereof. The ascorbate employed is preferably obtained from identical amounts of calcium ascorbate and magnesium ascorbate.

If necessary, one or both of the ingredients can be combined with coenzyme Q10 in a combined pharmaceutical composition or in separate pharmaceutical compositions, as outlined in U.S. Pat. No. 4,929,437.

According to the present invention, L-ascorbic acid or ascorbate or Mixture 1 is used for treating or preventing the vascular calcification, specifically the vascular calcification induced in patients by administration of statins.

The term "treating" in this context means "mitigating" or "reversing" or "reducing". The terms mixture 1, pharmaceutical composition mixture 1 or vascular calcification reducing pharmaceutical composition is used through out the application to represent mixture 1 or L ascorbic acid or ascorbate with or without statin.

Specifically, the calcification of vascular smooth muscle cells (SMC), more specifically human aortic smooth muscle cells (AoSMC) shall be prevented or mitigated. The present invention is specifically based on the positive effect of vitamin C on vascular SMC, human dermal fibroblasts (DF) as well as immortalized human fetal osteoblasts (FOB). The process of vascular calcification requires a phenotypic transformation of vascular smooth muscle cells (VSMC) into osteogenic cells.

The concomitant administration of at least one statin and mixture 1 or L-ascorbic acid or ascorbate to a patient is helpful for treating or preventing cardiovascular disease, for example coronary artery disease, cerebrovascular disease or peripheral vascular disease.

By applying the present invention, the increased calcification observed under long-term statin treatments can be mitigated, reversed or prevented. Thus, there is no need for a hypothetical interpretation that the statin-induced calcification could be beneficial or that there could be a beneficial macro-calcification, as opposed to detrimental micro-calcification.

Materials and Methods: All reagents were from Sigma-Aldrich (St. Louis, Mo., USA) except when indicated differently. Mixture 1 nutritional supplement was dissolved according to US Pharmacopea standard procedure (USP 2040 Disintegration and Dissolution of Dietary Supplements) as followed. Three recommended daily doses (nine tablets) were crushed and suspended in 900 ml 0.1 N HCl. Following one hour incubation in water bath incubator at 37° C. on an orbital shaker at 75 rpm, the supplement suspension was filtered through a 0.2 mcm sterile filter, and 1 ml aliquots were frozen and stored at 20° C. until use. The resulted Mixture 1 solution contained 19 mM ascorbic acid according to the manufacturer's specification.

Cell cultures: Normal human dermal fibroblasts (DF) and immortalized human fetal osteoblasts (hFOB) were supplied by ATCC (Manassas, Va., USA). Human aortic smooth muscle cells (AoSMC) were purchased from Cambrix (East Rutherford, N.J.) and used in experiments at 5 to 7 passages. Cell cultures were maintained in DMEM medium (ATCC) containing antibiotics and 5% fetal bovine serum (FBS, ATCC). In some experiments cells were incubated in pro-osteogenic medium, defined as 5% FBS/DMEM fortified with 5 mM beta-glycerophosphate with or without 25 mcM forskolin. All cell cultures were maintained at 37° C. and 5% $CO_2$ atmosphere. Cell viability was monitored with MTT assay.

Alkaline phosphatase activity assay in AoSMC: AoSMC were plated in 96 well plates and grown to confluent layer. Cells were incubated with ascorbic acid in growth medium for three days, 3 to 5 days in case of Mixture 1 experiments. Cells were washed with phosphate buffered saline (PBS) and supplemented with 50 mcl/well 25 mcg/ml 4-MUP (fluorescent ALP substrate, Sigma) in alkaline buffer (Sigma)/1% Triton X100 for 1 h at room temperature. Fluorescence was measured at 360/450 nm.

Calcium accumulation in extracellular matrix: AoSMC were seeded on fibronectin covered plastic plates at density 25,000 per square cm and grown to confluence for 5 to 7 days. Ascorbic acid was added to cells at indicated concentrations for 72 hours in DMEM supplemented with 2% FBS and cell-produced extracellular matrix was exposed by sequential treatment with 0.5% Triton X100 and 20 mM ammonium sulfate in phosphate buffered saline (PBS, Life Technologies) for 3 min each at room temperature. Plant-derived micronutrients suppress monocyte adhesion to cultured human aortic endothelial cell layer by modulating its extracellular matrix composition. J Cardiovasc Pharmacol 2008; 52:55-65. After four washes with PBS, ECM layers were solubilized by incubation in 0.6N HCl for 48 hours at 37° C. Calcium content in solubilized samples was measured with TECO Ca assay according to the manufacturer's protocol.

Expression of osteoblasts markers in human cultured cells: For the experiments AoSMC, DF and hFOB cells were seeded in separate 96 well plastic plates at density 25,000 per square cm and grown to confluence for 5 to 7 days. Tested compounds were added to cells at indicated concentrations for 72 hours in DMEM supplemented with 2% FBS. Cell layers were washed three times with PBS and fixed with 3% formaldehyde in PBS at 4° C. for one hour. Fixed cell layers were washed four times with PBS and treated with 1% BSA/PBS for one hour at RT. Immunoassay for osteogenic markers was done by sequential incubation with primary monoclonal antibodies (R&D Systems) in 1% BSA/PBS for 2 hours followed by 1 hour incubation with secondary goat anti-mouse IgG antibodies labeled with horse radish peroxidase (HRP). Retained peroxidase activity was measured after the last washing cycle (three times with 0.1% BSA/PBS) using TMB peroxidase substrate reagent (Rockland). Optical density was read with plate reader (Molecular Devices) at 450 nm and expressed as percentage of control cell samples incubated in unsupplemented 2% FBS/DMEM. To ensure a direct comparison of osteogenic markers expression on different cell types all pcell-covered plates were treated identical and simultaneously during immunoassay.

Statistical analysis: Results in figures are means±standard deviation (SD) from three or more repetitions from the most representative of at least two independent experiments. Differences between samples were estimated with a two-tailed Student's t-test using Excel software (Microsoft) and accepted as significant at p levels less than 0.05. The results in FIGS. 4A and 4B and FIGS. 5A and 5B are expressed as percentage of supplemented controls and presented as means±SD from six or more repetitions from the most representative of at least two independent experiments.

Cellular calcification process was investigated in human AoSMC cultured in a regular cell growth medium (5% FBS/DMEM) in the absence and presence of various amounts of ascorbic acid. The calcification process of AoSMC was evaluated by the activity of cellular alkaline phosphatase and calcium accumulation in the cell-produced extracellular matrix (FIG. 1).

The results show that supplementation of AoSMC medium with ascorbic acid up to 300 mcM resulted in a significant decrease in the level of extracellular calcium and lower activity of cellular alkaline phosphatase in dose-dependent manner. In the presence of 300 mcM ascorbate the extracellular Ca accumulation by AoSMC decreased by 20% and alkaline phosphatase activity by 80%.

Figure 2A:
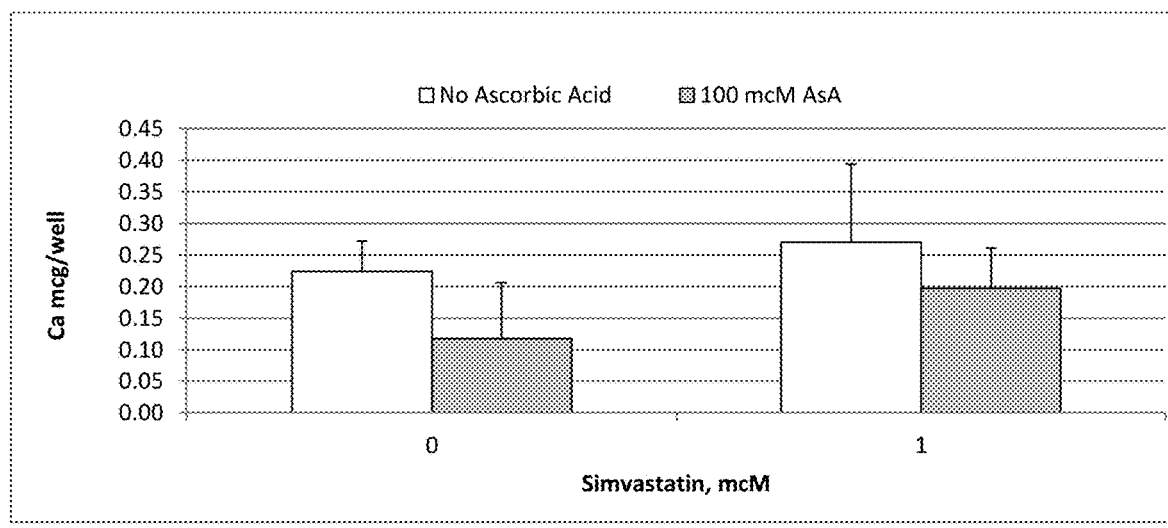
FIG. 2A shows the effects of Simvastatin on Ca accumulation in AoSMC culture without forskolin.

The results presented in FIG. 2A show that calcium accumulation in AoSMC layers was increased in the presence of simvastatin by 23%. However, concomitant presence of 100 mcM ascorbate calcium resulted in a 54% decrease of accumulated calcium to the value 0.2 mcg/well, which correlated with the values observed in cells not exposed to simvastatin.

Figure 2B:
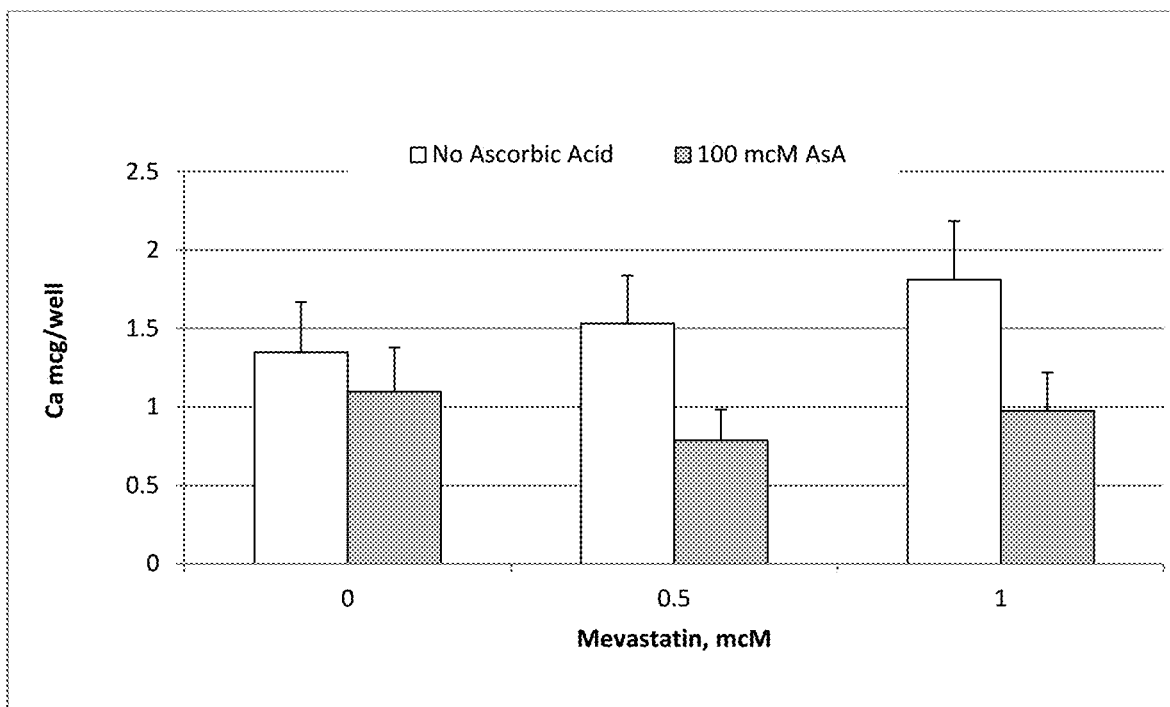
FIG. 2B shows the effects of mevastatin on Ca accumulation in AoSMC culture with 25 mcM forskolin.

The effect of ascorbate on calcium accumulation in AoSMC under enhanced pro-calcification condition (with forskolin) and in the presence of a statin (mevastatin) is presented in FIG. 2B. The results show that in the presence of 1 mM mevastatin calcium accumulation increased from 1.35 mcg/well in control to 1.8 mcg/well with mevastatin. However, when 100 mcM ascorbate was added, calcium accumulation decreased by 19% to below control (non-supplemented) values.

Figure 3A:
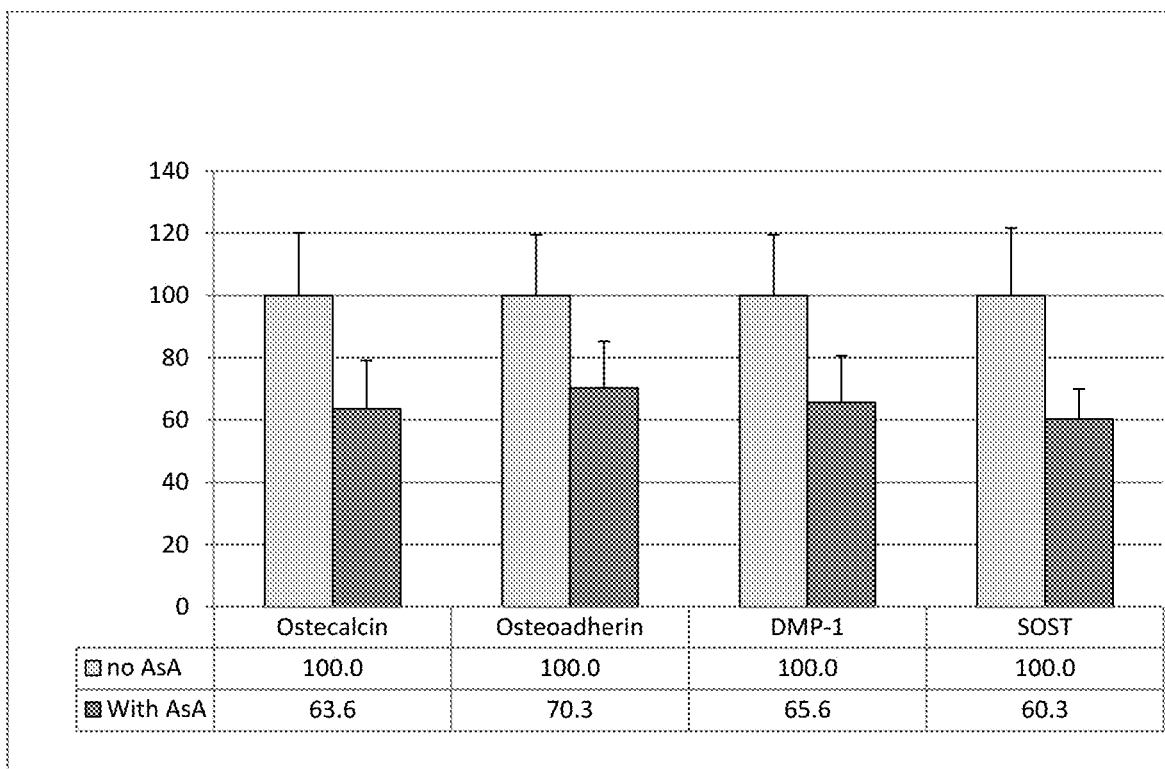
FIG. 3A shows the effects of 200 mcM ascorbate on osteoblast markers expression in human aortic SMC incubated for 4 weeks in osteogenic medium supplemented with 5 mM beta-glycerophosphate and 25 mcM forskolin.
Figure 3B:
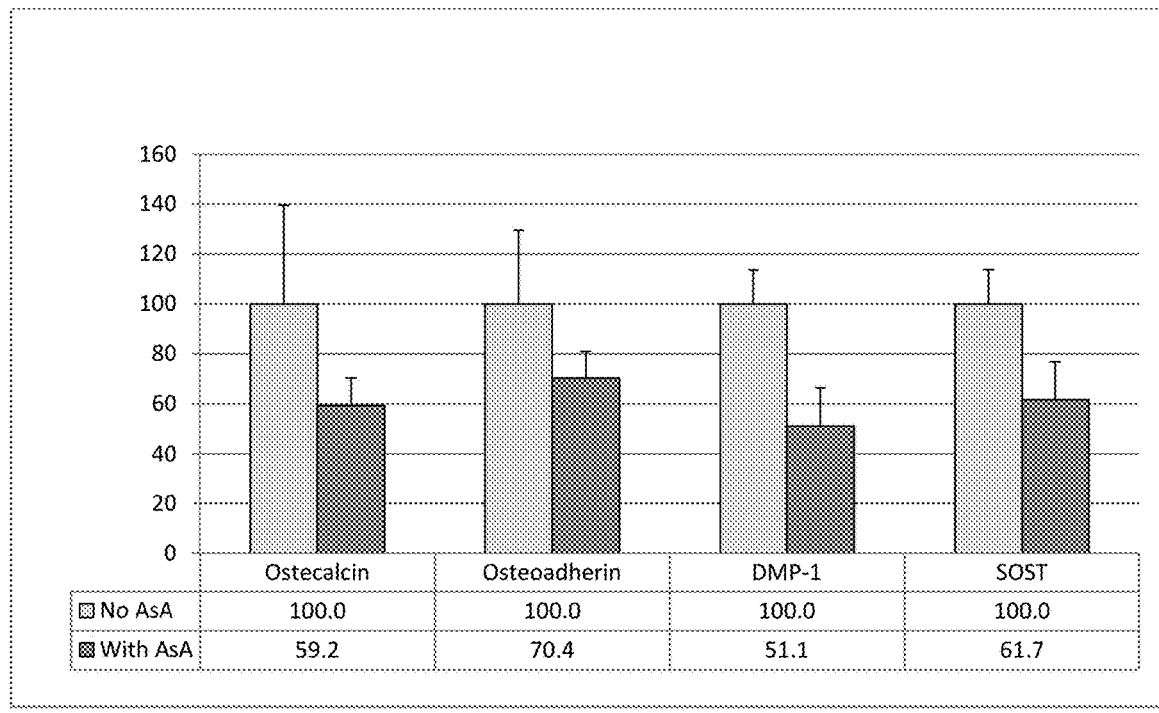
FIG. 3B shows effects of 200 mcM ascorbate on osteoblast markers expression in human dermal fibroblasts incubated for 4 weeks in osteogenic medium supplemented with 5 mM beta-glycerophosphate and 25 mcM forskolin.

In addition to SMC we studied the effect of ascorbate on cellular calcification process in human dermal fibroblasts (DF) and immortalized human fetal osteoblasts (FOB) by evaluating changes in the expression of different pro-osteogenic markers in these cells. The effects of ascorbate in different types of cells challenged with pro-osteogenic conditions such as by growing them in the medium supplemented with 5 mM beta-glycerophosphate and 25 mcM forskolin. The results show that expression of all tested osteogenic markers was significantly reduced by 100 mcM ascorbic acid supplementation in both AoSMC and DF cultures (FIGS. 3A and 3B). Ascorbic acid supplementation of hFOS osteoblasts in pro-osteogenic medium over four week period was cytotoxic. Corresponding data were omitted from the presentation.

We compared the levels of osteogenic markers expression in the test human cell types as presented in Table 1. The results indicate that in a regular growth medium, the expression of osteocalcin, osteoadherin, dentin matrix protein 1 (DMP-1) and sclerostin (SOST) were most prominent in osteoblasts cells (FOB) closely followed by fibroblasts (DF), except of DMP-1, expression of which in fibroblasts slightly overcame that of FOB cultures. Cellular expression of these four osteogenic markers in AoSMC cultured in regular growth medium was significantly (2 to 4 fold) less prominent than in FOB and DF cultures.

In the present tests we demonstrated that ascorbic acid tested up to 300 mcM concentrations can reduce calcium accumulation in ECM produced by AoSMC. This effect was accompanied by the blockage of SMC osteogenic transformation as indicated by changes in specific metabolic parameters, such as reduction in cellular alkaline phosphatase activity, and cellular expression of osteoblast marker proteins. A high level of serum alkaline phosphatase (ALP) is associated with an increased risk of mortality and myocardial infarction. ALP hydrolyses inorganic pyrophosphate, which is a strong inhibitor of calcium phosphate deposition.

TABLE 1

Levels of osteogenic markers expression in the test human cell types:

| Cell type | | Osteocalcin | | Osteoadherin/ OSAD | | DMP-1 | | SOST/ Sclerostin | |
|---|---|---|---|---|---|---|---|---|---|
| | | mean | sd | mean | sd | mean | sd | mean | sd |
| AoSMC | Plain Medium | 0.288 | 0.047 | 0.259 | 0.025 | 0.412 | 0.063 | 0.212 | 0.030 |
| | Osteogenic Medium | 0.429 | 0.086 | 0.315 | 0.061 | 0.569 | 0.111 | 0.289 | 0.063 |
| hDF | Plain Medium | 1.087 | 0.051 | 0.889 | 0.093 | 1.137 | 0.089 | 0.657 | 0.058 |
| | Osteogenic Medium | 0.614 | 0.242 | 0.403 | 0.119 | 0.851 | 0.116 | 0.374 | 0.051 |
| FOS | Plain Medium | 1.206 | 0.288 | 1.493 | 0.147 | 0.819 | 0.307 | 0.956 | 0.197 |
| | Osteogenic Medium | 1.003 | 0.207 | 1.049 | 0.213 | 0.786 | 0.078 | 0.633 | 0.126 |

Under physiological conditions (cells incubated in regular cell culture medium) expression of osteocalcin, osteoadherin and SOST/sclerostin were the highest in hFOS cultures and the lowest in hAoSMC cultures. Expressions of these markers were intermediate in hDF cultures. Under physiological conditions (cells incubated in regular cell culture medium) expression of DMP-1 was the highest in hDF cultures and the lowest in hAoSMC cultures. Expression of DMP-1 was intermediate in hFOS cultures. Cell supplementation with pro-osteogenic medium as compared to regular medium caused stimulation of all tested osteomarkers in AoSMC cultures. In contrast, pro-osteogenic medium supplementation caused an inhibition of all tested osteogenic markers in hDF and hFOS cultures.

Figure 4A:
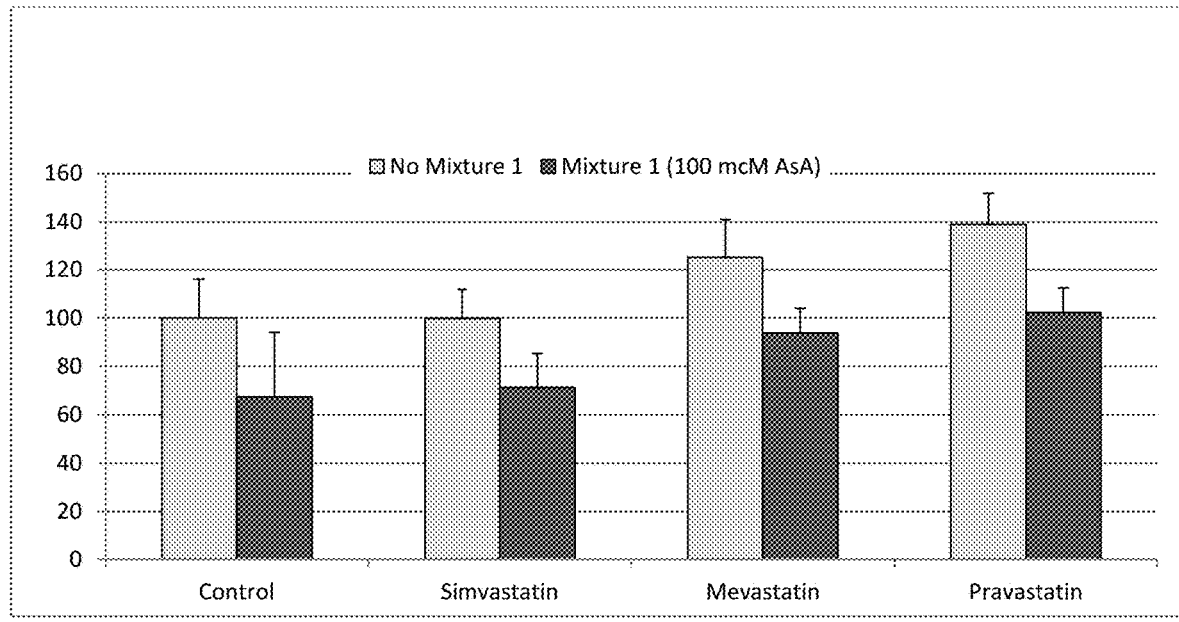
FIG. 4A shows effects of 1 mcM statins and Mixture 1 (at 100 mcM ascorbate) on alkaline phosphatase activity in AoSMC supplemented in plain 5% FBS/DMEM for four days. 90 min incubation with MSU substrate.
Figure 4B:
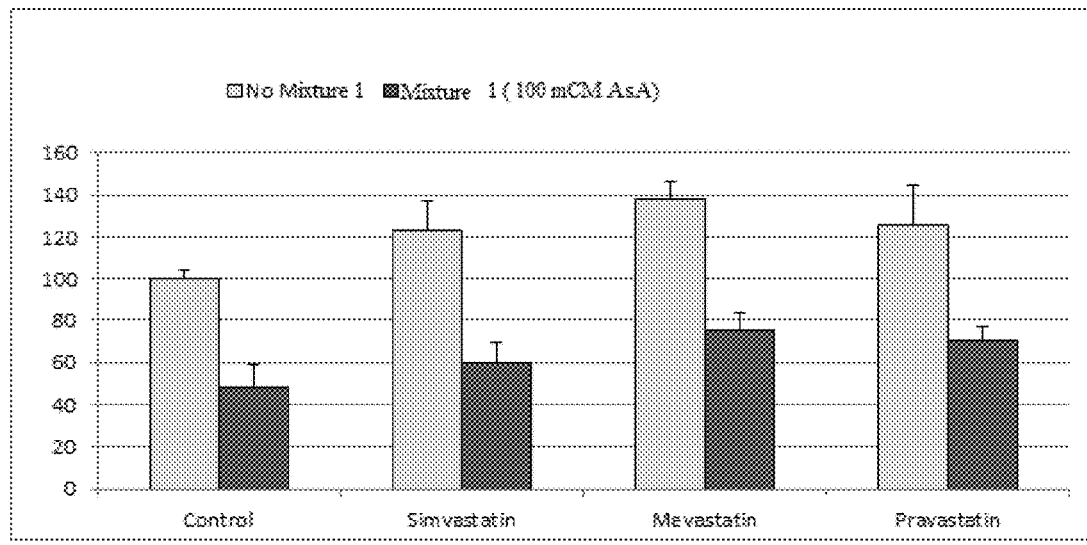
FIG. 4B shows the effects of 1 mcM statins and Mixture 1 (and 100 mcM ascorbate) on alkaline phosphatase activity in AoSMC supplemented in 5 mM b-GP and 25 mcM forskolin for four days. 95 min incubation with MSU substrate.

Description of the results presented on FIG. 4 (A and B) and FIG. 5 (A and B) shows cellular calcification process was investigated in human aortic smooth muscle cells (AoSMC) cultured in cell culture medium in the absence and presence of various statins: simvastatin, mevastatin and pravastatin used at 1 mcM concentration each. The calcification process of AoSMC was evaluated by the activity of cellular alkaline phosphatase (ALP). The study assessed the effects of Mixture 1 (micronutrient combination containing ascorbate) and ascorbate individually under standard (5% FBS/DMEM) and pro-calcification conditions (5% FBS/DMEM supplemented with 5 mM beta-glycerophosphate (b-GP) and 25 mcM forskolin—FIG. 4B).

The results on FIG. 4A show that ALP activity of AoSMC under normal cell culture condition was not affected by simvastatin but it increased in the presence of mevastatin by 25%, and pravastatin by 39% compared to control. Addition of Mixture 1 at a concentration equivalent to 100 mcM ascorbate resulted in lowering of ALP activity. As such ALP was lower by 33% in control and by 29%, 25%, 27% in the presence of simvastatin, mevastatin and pravastatin, respectively. A combination of pravastatin and Mixture 1 resulted in lowering calcification process to the level observed in control (unsupplemented). Mixture 1 in the presence of simvastatin and mevastatin decreased ALP activity below control values. The most effective in lowering APL activity was a combination of Mixture 1 with simvastatin—33% below control value and almost equal to the effect of a Mixture 1 applied alone.

The results presented on FIG. 4B show that under pro-calcification condition (5 mM b-GP and 25 mcM forskolin) the presence of simvastatin resulted in an increase in ALP activity by 22%, with mevastatin by 39% and pravastatin by 25% compared to control. By adding Mixture 1 in the presence and absence of statins, the ALP activity decreased by 52% in control and in the presence of simvastatin, mevastatin and pravastatin, by 52%, 45%, 44% respectively compared to no Mixture 1 values. Similarly to normal cell culture condition, the efficacy of Mixture 1 in lowering ALP activity was the highest when combined with Simvastatin (40% compared to control). Mixture 1 in combination with all test statins significantly lowered APL activity to below control levels. The significant ALP lowering effect of Mixture 1 was compared to ascorbic acid used individually at 300 mcM concentration, which is 3 times higher than its equivalent amount contained in Mixture 1 formulation.

Figure 5A:
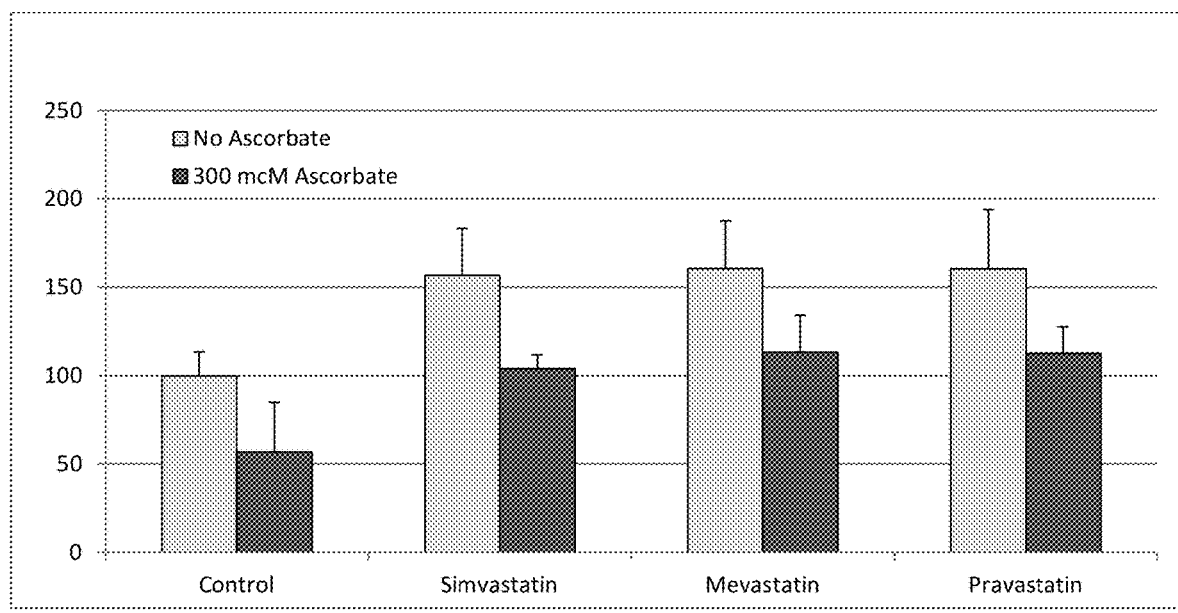
FIG. 5A shows the effects of 1 mcM statins and 300 mcM ascorbate on alkaline phosphatase activity in AoSMC supplemented in plain 5% FBS/DMEM for five days.

The results on FIG. 5A show that supplementation of AoSMC medium with 300 mcM ascorbic acid in the presence and absence of test statins resulted in a significant decrease in the activity of cellular alkaline phosphatase (ALP). Under normal culture medium condition, ascorbic acid decreased alkaline phosphatase activity by about 43%. In the presence simvastatin ALP activity was higher by 57% and decreased to control level after addition of 300 mcM ascorbate. In a similar way mevastatin and pravastatin increased ALP activity by 61% and 60%, respectively. These stimulatory effects were decreased by 29% and 30%, respectively, in the presence of ascorbic acid.

Figure 5B:
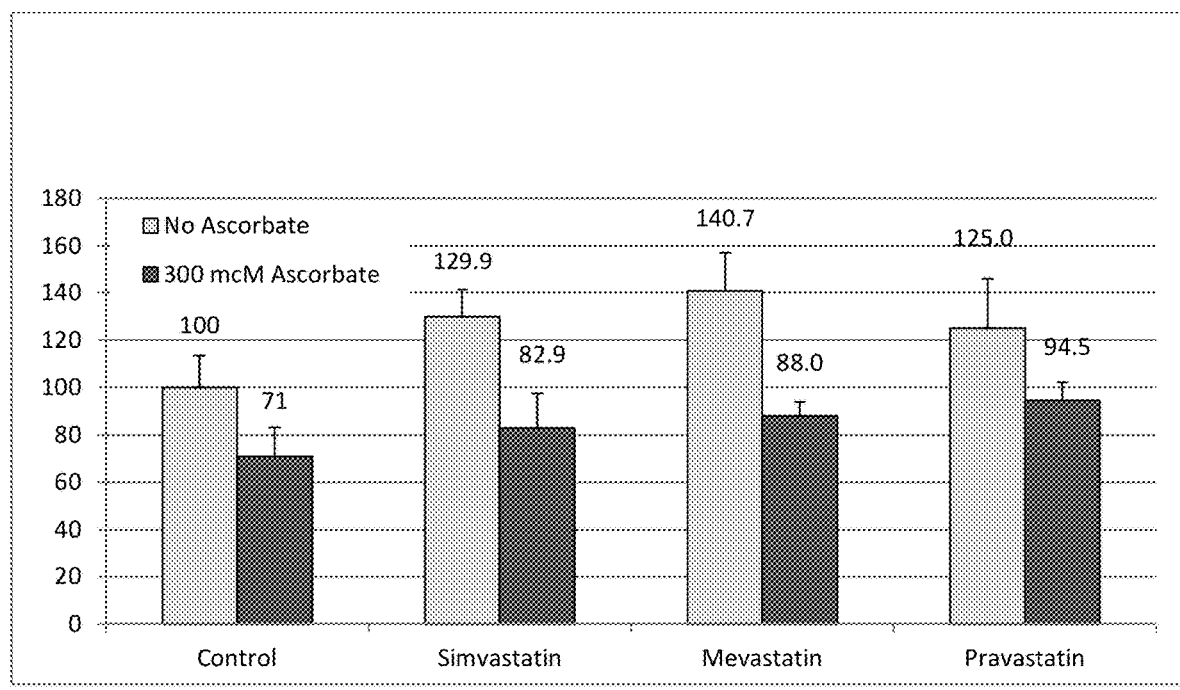
FIG. 5B shows the effects of 1 mcM statins and 300 mcM ascorbate on alkaline phosphatase activity in AoSMC supplemented in 5% FBS/DMEM/5 mM b-GP, 25 mcM forskolin for five days.

The results on FIG. 5B show that under pro-calcification conditions statins caused an increase of 30%, 41% and 25% of the stimulation of ALP activity for simvastatin, mevastatin and pravastatin, respectively. Simultaneous supplementation with ascorbate resulted in a decrease in ALP activity by 36%, 37% and 24% for simvastatin, mevastatin and pravastatin containing samples, respectively. Under the same experimental conditions, ascorbic acid added to AoSMC in the absence of statins decreased ALP activity by 29%.

Industrial Use

Thus, in this study we prove that mixture 1 and/or vitamin C plays a decisive role in regulating the cellular and extracellular architecture and function inside the vascular wall. With optimum availability of ascorbate, the integrity and stability of the vascular wall would be provided, above all, by an optimum synthesis of collagen and other ECM molecules.

What is claimed is:

1. A vascular calcification reducing pharmaceutical composition, consisting of:
   a Vitamin C, Vitamin E, Vitamin B1, Vitamin B2, Vitamin B3, Vitamin B5, Vitamin B6, Vitamin B12, Folic acid, Biotin, L-carnitine, Betaine and statin.
2. The vascular calcification reducing pharmaceutical composition of claim 1, wherein a physiological dose after calculation for the mammal for the vascular calcification reducing pharmaceutical composition amount are in a range of Vitamin C—300-1000.2 mg, Vitamin E—27.5 mg-82.5 mg, Vitamin B1—3.3 mg-9.9 mg, Vitamin B2—3.3 mg-9.9 mg, Vitamin B3—115 mg-350.1 mg, Vitamin B5—16.7 mg-50.1 mg, Vitamin B6—3.3 mg-9.9 mg, Vitamin B12—10 μg-30 μg, Folic acid—133.3 ug-399.9 μg, Biotin—33.3 ug-99.9 μg, L-carnitine—33.3 mg-99.9 mg, Betaine—23.3 mg-69.9 mg and the one statin from 5 mg to 100 mg.

3. The vascular calcification reducing pharmaceutical composition according to claim 1, wherein the statin is selected from the group consisting of an atorvastatin, cerivastatin, fluvastatin, lovastatin, mevastatin, pitavastatin, pravastatin, rosuvastatin, simvastatin, or mixtures thereof.

4. The vascular calcification reducing pharmaceutical composition according to claim 1, wherein the Vitamin C is in ascorbate form, wherein the ascorbate is selected from water soluble or lipid soluble ascorbates, or mixtures thereof.

5. The vascular calcification reducing pharmaceutical composition according to claim 1, wherein the ascorbate is selected from a calcium ascorbate, magnesium ascorbate, sodium ascorbate, ascorbyl phosphate, ascorbyl palmitate or mixtures thereof.

6. A method of reducing vascular calcification induced due to a statin consumption in a mammal by administering a vascular calcification reducing pharmaceutical composition consisting of: a Vitamin C, Vitamin E, Vitamin B1, Vitamin B2, Vitamin B3, Vitamin B5, Vitamin B6, Vitamin B12, Folic acid, Biotin, L-carnitine, Betaine and statin.

7. The method of claim 6, wherein a physiological dose after calculation for the mammal for the vascular calcification reducing pharmaceutical composition amount are in a range of Vitamin C—300-1000.2 mg, Vitamin E—27.5 mg-82.5 mg, Vitamin B1—3.3 mg-9.9 mg, Vitamin B—3.3 mg-9.9 mg, Vitamin B3—115 mg-350.1 mg, Vitamin B5—16.7 mg-50.1 mg, Vitamin B6—3.3 mg-9.9 mg, Vitamin B12—10 μg-30 g, Folic acid—133.3 ug-399.9 μg, Biotin—33.3 ug-99.9 μg, L-carnitine—33.3 mg-99.9 mg, Betaine—23.3 mg-69.9 mg and the one statin from 5 mg to 100 mg.

8. The method according to claim 6, wherein the statin is selected from the group consisting of an atorvastatin, cerivastatin, fluvastatin, lovastatin, mevastatin, pitavastatin, pravastatin, rosuvastatin, simvastatin, or mixtures thereof.

9. The method according to claim 6, wherein the Vitamin C is in ascorbate form, wherein the ascorbate is selected from water soluble or lipid soluble ascorbates, or mixtures thereof.

10. The method according to claim 6, wherein the ascorbate is selected from a calcium ascorbate, magnesium ascorbate, sodium ascorbate, ascorbyl phosphate, ascorbyl palmitate or mixtures thereof.

* * * * *